United States Patent [19]

Eriksen et al.

[11] Patent Number: 5,191,151
[45] Date of Patent: Mar. 2, 1993

[54] USE OF SILVER-EXCHANGED IONOMER MEMBRANES FOR GAS SEPARATION

[75] Inventors: Odd I. Eriksen; Elin Aksnes; Ivar M. Dahl, all of Oslo, Norway; Fu-Ming Lee, Bartlesville, Okla.

[73] Assignee: Phillips Petroleum Company, Bartlesville, Okla.

[21] Appl. No.: 809,828

[22] Filed: Dec. 18, 1991

[51] Int. Cl.$^5$ .......................... C07C 7/144; C07C 7/10
[52] U.S. Cl. .................................... 585/818; 585/843; 585/844; 55/16
[58] Field of Search ...................... 585/818, 843, 844; 55/16

[56] References Cited

U.S. PATENT DOCUMENTS

| | | | |
|---|---|---|---|
| 3,758,603 | 9/1973 | Steigelmann et al. | 260/677 A |
| 3,758,605 | 9/1973 | Hughes et al. | 260/677 A |
| 3,865,890 | 2/1975 | Steigelmann et al. | 55/16 |
| 3,940,469 | 2/1975 | Steigelmann et al. | 264/177 F |
| 3,980,605 | 9/1976 | Steigelmann et al. | 260/30.8 DS |
| 4,039,499 | 8/1977 | Steigelmann et al. | 260/29.6 NR |
| 4,047,908 | 9/1977 | Steigelmann et al. | 55/158 |
| 4,614,524 | 9/1986 | Kraus | 55/16 |
| 4,731,263 | 3/1988 | Martin et al. | 427/385.5 |

FOREIGN PATENT DOCUMENTS

2169301 12/1984 United Kingdom.

OTHER PUBLICATIONS

W. Featherstone et al., "Silver-Hydrocarbon Complexes", Journal of the Chemical Society, Oct. 1964, pp. 5235-5242.

R. S. Yeo et al., "Swelling Behavior of Nafion and Radiation-Grafted Cation Exchange Membranes", Journal of Membrane Science 9(1981), pp. 273-283.

"Materials Science of Synthetic Membranes", ACS Symposium Series 269, 1985, Chapter 18, p. 366.

R. S. Yeo, "Swelling Studies of Perfluorinated Ionomer Membranes", Journal of Applied Polymer Science, vol. 32 (1986), pp. 5733-5741.

J. Pellegrino et al., "Facilitated Transport of $CO_2$ Through Highly Swollen Ion-Exchange Membranes...", Gas Separ. and Purific., vol. 2, 1988, pp. 126-130.

M. D. Heaney et al., "Increased Facilitated Transport Related to Microstructural Changes in Heat-Treated Ion-Exchange Membranes", Journal of Membrane Science 47 (1989), pp. 143-161.

C. A. Koval et al., "Styrene/Ethylbenzene Separation Using Facilitated Transport Through Perfluorosulfonate Ionomer Membranes", Industrial Engineer. Chem. Research 28 (1989), pp. 1020-1024.

T. Kanno et al., "Enhancement of the Permeabilities of Ethylene and Propylene Gases in Nation-Ag Composite", J. Chem. Soc. Chem. Commun. No. 19, 1989, pp. 1854-1855.

*Primary Examiner*—Anthony McFarlane
*Assistant Examiner*—Nhat D. Phan
*Attorney, Agent, or Firm*—K. K. Brandes

[57] ABSTRACT

A process for separating $C_2$-$C_4$ alkenes from $C_1$-$C_6$ alkanes comprises the presence of water vapor in the alkene/alkane feed and the use of an $Ag^+$-exchanged sulfonated copolymer of tetrafluoroethylene and perfluorovinyl ether having been prepared by one of several specific ion-exchange methods.

51 Claims, No Drawings

USE OF SILVER-EXCHANGED IONOMER MEMBRANES FOR GAS SEPARATION

BACKGROUND OF THE INVENTION

This invention relates to a process for separating gaseous alkenes (in particular ethylene) from gaseous alkanes (in particular ethane) employing silver-exchanged ionomer membranes.

The use of membranes of ion-exchange polymers (ionomers) for alkene/alkane separation is known. Particularly effective ionomers are sulfonated copolymers of tetrafluoroethylene and perfluorovinyl ether. These copolymers are commercially available, e.g., from Du Pont de Nemours and Company, Wilmington, DE, under various Nafion ® product designations. The present invention is directed to the use of $Ag^+$-exchanged membranes of these ionomers for separating gaseous alkenes from gaseous alkanes, in particular ethylene from ethane.

SUMMARY OF THE INVENTION

It is an object of this invention to use membranes of a silver-exchanged sulfonated copolymer of tetrafluoroethylene and perfluorovinyl ether in a process of separating gaseous $C_2$-$C_4$ alkenes from gaseous alkanes. It is a particular object of this invention to provide a process for separating ethylene from ethane employing said membranes. Further objects and advantages will become apparent from the detailed disclosure and the appended claims.

In accordance with this invention, in a process for separating at least one alkene (monoolefin) containing 2 to 4 carbon atoms per molecule (in particular ethylene) from at least one alkane (paraffin) containing 1 to 6 carbon atoms per molecule (in particular ethane) contained in a gaseous feed by means of an ionomer membrane, the improvements comprise:

the presence of water vapor in said gaseous feed, and the use of a silver-exchanged ionomer membrane having been prepared by the preparation method comprising the steps of:

(a) contacting (i) an ionomer membrane of a copolymer of tetrafluoroethylene and a perfluorovinyl ether containing a terminal sulfonic acid group with (ii) a solution of at least one alkali metal compound, under such conditions as to obtain an alkali-metal-exchanged ionomer membrane;

(b) contacting the thus-obtained alkali-metal-exchanged ionomer membrane with a liquid comprising at least one alcohol containing from 2 to 20 carbon atoms and from 1 to 5 hydroxyl groups per molecule, under such conditions as to obtain a swollen alkali-metal-exchanged ionomer membrane; and (c) treating the thus-obtained swollen alkali-metal-exchanged ionomer membrane with a solution containing at least one silver compound, under such conditions as to at least partially (preferably substantially) replace alkali metal ions with silver ions in said ionomer membrane.

Preferably, the above-outlined membrane preparation method comprises the additional step (a1) of separating the alkali-metal-exchanged ionomer membrane obtained in step (a) from the solution of at least one alkali metal compound used in step (a). Also preferably, the above-outlined preparation method comprises the additional step (a2) of heating the separated alkali-metal-exchanged membrane obtained in step (a1) at a temperature in the range of from about 100° to about 350° C. for a period of time of about 1 minute to about 3 hours, and thereafter rapidly cooling the thus-heated membrane to a temperature of about 10°-50° C. (more preferably a rate of about 1°-5° C. per second). In another preferred embodiment, the above-outlined preparation method comprises the additional step (b1) of separating the swollen alkali-metal-exchanged ionomer membrane obtained in step (b) from the alcohol(s) used in step (b). A further preferred embodiment comprises the additional step (b2) of immersing the swollen alkali-metal-exchanged ionomer membrane obtained in step (b1) in water or, alternatively, in a dilute aqueous solution of an alkali metal compound, before step (c) is carried out. Preferably, the above-outlined preparation method comprises the additional step (c1) of separating the silver-exchanged ionomer membrane obtained in step (c) from the solution containing at least one silver compound.

Also in accordance with this invention, in a process for separating at least one alkene containing 2 to 4 carbon atoms per molecule (in particular ethylene) from at least one alkane containing 1 to 6 carbons per molecule (in particular ethane) contained in a gaseous feed by means of an ionomer membrane, the improvements comprise:

the presence of water vapor in said gaseous feed, and the use of a silver-exchanged ionomer membrane having been prepared by the preparation method consisting essentially of the steps of:

(A) contacting (i) an ionomer membrane of a copolymer of tetrafluoroethylene and a perfluorovinyl ether containing a terminal sulfonic acid group with (ii) a solution consisting essentially of at least one alkali metal compound and water, under such conditions as to obtain an alkali-metal-exchanged ionomer membrane; and (B) treating the alkali-metal-exchanged ionomer membrane obtained in step (A) with a solution consisting essentially of at least one silver compound and water, under such conditions as to obtain a substantially silver-exchanged ionomer membrane.

Further in accordance with this invention, in a process for separating at least one alkene containing 2 to 4 carbon atoms per molecule (in particular ethylene) from at least one alkane containing 1 to 6 carbon atoms per molecule (in particular ethane) contained in a gaseous feed by means of an ionomer membrane, the improvements comprise:

the presence of water vapor in said gaseous feed, and the use of a silver-exchanged ionomer membrane having been prepared by the preparation method comprising the steps of (1) mixing ($\alpha$) a solution of a copolymer of tetrafluoroethylene and a perfluorovinyl ether containing a terminal sulfonic acid group and ($\beta$) at least one silver compound, under such conditions as to obtain a solution comprising a silver-exchanged copolymer; and (2) coating a porous support material with the solution obtained in step (1).

DETAILED DESCRIPTION OF THE INVENTION

The ion-exchange polymer (ionomer) material employed in step (a) or, alternatively, in step (A) or, alternatively, in step (1) of the the preparation methods outlined above consists essentially of a copolymer of tetrafluoroethylene and a perfluorovinyl ether containing a terminal sulfonic acid (—SO₃H) group. These ionomer polymer materials are well known and have been described in various publications, such as Kirk Othmer Encyclopedia of Chemical Technology, Third Edition, 1984, Supplemental Volume, pages 559 and 592–595; Chemie-Ing. Techn. 47, 617 (1975); and U.S. Pat. No. 4,731,263. The monomer repeat unit of the ionomer material used in step (a) or, alternatively, in step (A) or, alternatively, in step (1) can be represented by the following structural formula:

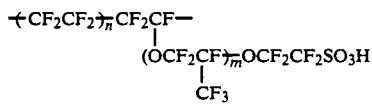

wherein n is a whole number which is preferably in the range of from about 5 to about 12, and m is a whole number which is preferably in the range of from about 1 to about 3 and, more preferably, is 1. The ionomer preferably has an equivalent weight of about 500–2000, more preferably 1000–1500, wherein the equivalent weight is defined as the weight of the ionomer in grams which will neutralize one gram-equivalent of a base (such as NaOH).

The ionomer material described above can be converted to an ionomer membrane, which is to be used in step (a), or, alternatively, in step (A) by any of the well known techniques, such as extrusion, biaxial drawing, casting (from an ionomer solution), and the like. The thickness of the membrane generally is in the range of from about 0.1 to about 400 microns (micrometers), preferably about 150–350 microns. The membrane can be applied either as an unsupported film (generally placed between two metal screens) or as a film deposited on any suitable porous support material, such as a glass frit or a porous polymer material or a honeycomb monolith ceramic support (e.g., a cordierite honeycomb monolith material which is commercially available). Hollow fibers (commercially available, generally having an outer diameter of about 400–900 microns and a wall thickness of about 50–150 microns) of the ionomer material can also be used as the ionomer membrane in step (a) or, alternatively, step (A).

Any suitable solution of alkali metal compound(s) can be employed in step (a) or, alternatively, step (A) of the membrane preparation methods outlined above. Generally, the solution is either an aqueous solution (preferred) or an alcoholic solution or any other solution containing a polar solvent capable of dissolving the alkali metal compound, preferably alkali metal hydroxide, in particular NaOH. The concentration of the alkali metal compound in the contacting solution of step (a) or, alternatively, step (A) generally ranges from about 0.02 mole/l to about 2 mole/l, and preferably is about 0.1–0.5 mole/l.

Step (a) or, alternatively, step (A) can be carried out in any suitable manner. Generally, the membrane is completely immersed in the alkali metal compound solution and is heated in the solution at a temperature of about 30°–100° C. (more preferably under reflux conditions), for a time period sufficient to substantially convert the protonic sulfonic acid groups to the anionic form (—SO₃⁻), with alkali metal cations as counterions. The time of contact between the ionomer membrane and the alkali metal compound solution generally ranges from about 0.5 to about 50 hours (depending on the concentration of the solution, the temperature during the contacting of the membrane with the solution, and the extent of agitation during the contacting of the membrane with the solution). Preferably, the time of contact between membrane and solution is about 2–5 hours.

Preferred separation step (a1) can be carried out in any suitable manner. In most cases, the membrane is simply removed from the alkali metal compound solution. Optionally, the membrane is rinsed (washed), preferably with an alcohol or with water, so as to remove adhered alkali metal compound solution therefrom.

Preferred heating/quenching step (a2) can be carried out in any suitable manner, either in a free oxygen containing atmosphere (such as air) or in an inert atmosphere (such as He or Ar or N₂). First, the membrane obtained in step (a1) is heated to a temperature of about 100° C. to about 350° C., preferably a temperature of about 330°–350° C., for about 1 minute to about 3 hours (preferably about 1–2 hours). The thus-heated membrane is then rapidly cooled (quenched), preferably at a rate of about 1°–5° C. per second (more preferably about 2°–4° C. per second) to a final temperature of about 10°–50° C. (preferably about 15°–30° C.).

Swelling step (b) is carried out with the membrane obtained in step (a) or, alternatively, step (a1) or, alternatively, step (a2). The alkali metal-exchanged membrane is treated with an alcohol which generally contains 2–20 carbon atoms and about 1–5 hydroxyl groups per molecule. Non-limiting examples include ethanol, n-propanol, isopropanol, 1-butanol, 2-butanol, t-butanol, pentanols, hexanols, cyclohexanol, heptanols, cycloheptanol, octanols, methylcycloheptanols, decanols, dodecanols, ethylene glycol, 1,3-propylene glycol, isopropylene glycol, butanediols (such as 1,4-butanediol, 2,4-butanediol), pentanediols, hexanediols, octanediols, decanediols, dodecanediols, glycerin, 1,2,3,4-tetrahydroxybutane, diethylene glycol, triethylene glycol, tetraethylene glycol, pentaethylene glycol, diisopropylene glycol, triisopropylene glycol, tetraisopropylene glycol, pentaisopropylene glycol, butylcarbitol (monobutyl ether of diethylene glycol), and the like, and mixtures of two or more of these alcohols. Preferred are polyhydric alcohols (i.e., alcohols with 2 or more OH groups per molecule). Presently more preferred is glycerine (also called glycerol). Generally, the alcohol is used without a diluent, but it is in the scope of this invention to have a minor amount of a diluent (such as water) present.

Step (b) can be carried out in any suitable manner. Generally, the membrane obtained in step (a) or, alternatively, step (a1), or alternatively, step (a2), is immersed in the alcohol(s) for at least about 0.1 hour, preferably for a period of time in the range of from about 1 hour to about 50 hours, more preferably about 20–30 hours. Any suitable temperature at which the alcohol is liquid can be employed in the swelling step. Preferably, the temperature is in the range of from about 75° C. to the normal boiling point (measured at 1 atm.) of the alcohol. When glycerin is employed as alcohol, the preferred temperature of swelling step (c) is in the range of about 200°–290° C. (more preferably about 225°–230° C.). Generally, the pressure in swelling step (b) is approximately atmospheric (1 atm).

Separating step (b1) can be carried out by any suitable means. Generally, the swollen ionomer membrane is simply removed from the alcohol (which preferably has been cooled to about room temperature). It is preferred (but not necessary) to wipe or rinse adhered alcohol droplets from the surface of the swollen membrane after it has been removed from the alcohol.

It is further preferred to include a washing step (b2) which comprises immersing the swollen membrane in water or, alternatively, an aqueous solution (generally about 0.1-2 molar) of an alkali metal compound (such as $NaNO_3$, NaOH, $NaBF_4$), generally at a temperature of about 15°-30° C. for a period of about 0.5-50 days. When an aqueous solution of alkali metal compound is used in step (b2), it is preferred to rinse the membrane with water at the completion of step (b2).

Silver ion-exchange step (c) can be carried out with the swollen ionomer membrane obtained in step (b) or, alternatively, step (b1) or, alternatively, step (b2) in any suitable manner. Generally, the swollen membrane is immersed in a solution (preferably aqueous) which contains at least one ionizable silver compound, such as AgF, $AgHSO_4$, $Ag_2SO_4$, $AgNO_3$, $AgClO_4$, $AgBF_4$ $AgCH_3CO_2$ (Ag acetate), $AgCF_3CO_2$, $AgCF_3SO_3$, and the like, or a mixture of two or more of these silver compounds. Presently preferred are $AgNO_3$ or $AgClO_4$ or $AgBF_4$ or mixtures thereof. Instead of immersing the membrane in a solution containing $Ag^+$ ions, the membrane can also be coated with the solution, or the silver ion containing solution can be sprayed onto the membrane. However, these latter methods are presently less preferred. It is preferred to carry out silver ion-exchange step (c) in the substantial absence of sunlight. Optionally, $H_2O_2$ can also be present in step (c) so as to reoxidize elemental silver which may have inadvertently been formed.

Any suitable silver concentration in the $Ag^+$ ion-exchange solution can be employed in step (c). Generally, the concentration is in the range of about 0.5 to about 6 g-equivalents $Ag^+$ per liter solution. The weight ratio of the $Ag^+$ ion-exchange solution to the swollen membrane in step (c) is such as to ensure a substantial (preferably complete) exchange of alkali metal ions contained in the swollen alkali-metal-exchanged ionomer membrane by silver ions, and will generally depend on the $Ag^{30}$ concentration of the solution and the total exposed surface and the thickness of the membrane. It is within the scope of this invention to incorporate an excess of $Ag+$ ions into the swollen ionomer membrane, i.e., more $Ag^+$ ions than are necessary to replace all alkali metal ions bound to $-SO_3^-$ groups in the ionomer membrane. Generally, the temperature in step (c) is about 10°-50° C. (preferably about 15°-30° C.), and the time of contact between the $Ag^+$ ion containing solution and the membrane is in the range of from about 1 hour to about 80 hours (preferably about 40-50 hours). Preferably, exposure to intensive sunlight is avoided (so as to prevent formation of elemental silver).

Preferred separation step (c1), can be carried out after the ion-exchange step (c), especially if step (c) is carried out by immersing the membrane in the $Ag+$ ion containing solution. The optional separation steps after step (c) can be carried out in a manner similar to separation steps (a1) and (b1), described above. The thus-separated $Ag^+$-exchanged membrane can be washed with a suitable liquid in optional step (c2), e.g., with water or methanol. It is preferred to wipe liquid droplets from the surface of the $Ag^+$-exchanged membrane obtained in step (c) or, alternatively, step (c1) or, alternatively, step (c2). It is, however, not preferred to extensively dry the $Ag^+$-exchanged ionomer membrane (e.g., by heating or by exposure to vacuum conditions), since the membrane is used for gas separations employing wet feed gases.

Preparation step (A) of the second embodiment of this invention can be carried out in essentially the same manner as step (a) employing an aqueous solution of at least one alkali metal compound. Preparation step (B) can be carried out with an aqueous solution of at least one silver compound in essentially the same meanner as step (c), except that the alkali-metal-exchanged membrane obtained in step (A) is used. The solutions used in steps (A) and (B) are essentially free of alcohols. It is within the scope of this invention to wash the $Ag^+$-exchanged ionomer membrane obtained in step (B) with water, and to wipe liquid droplets from the $Ag^+$-exchanged ionomer membrane obtained in step (B).

In preparation step (1) of the third embodiment of this invention, a solution of the ionomer material described above in any suitable solvent(s) is mixed with silver compound(s) in any suitable manner so as to obtain a solution of a silver-exchanged ionomer material. Non-limiting examples of silver compounds are essentially the same as those employed in ion-exchange step (c), described above. Non-limiting examples of suitable solvents for the ionomer material include the alcohols recited above for step (b), optionally in admixture with water (such as about 1-20 weight-% $H_2O$). Examples of other liquids which can also be employed as solvents for the ionomer material include those recited in U.S. Pat. No. 4,731,263, such as ethylene glycol, dimethylsulfoxide, sulfolane, N,N-dimethylformamide, N-methyl-2-pyrrolidone, butyrolactone, dimethylacetamide, triphenylphosphate and the like, and mixtures thereof, optionally in admixture with water. Generally, the ionomer concentration in the solution employed in step (1) is in the range of about 0.1 to about 10 weight-% ionomer material. It is preferred to carry out mixing step (1) for about 0.1-10 hours, more preferably for about 1-3 hours. The temperature in step (1) generally is about 10°-100° C., preferably about 20°-50° C.

Generally, the relative amount of the silver compound(s) employed in step (1) is such as to provide a ratio of g-equivalents of silver to g-equivalents of $-SO_3H$ groups (present in the ionomer material) in the range of about 0.5:1 to about 50:1, preferably about 1:1 to about 40:1. It is within the scope of this invention to incorporate an excess of $Ag^+$ ions into the ionomer material, i.e., more $Ag^+$ ions than are necessary to replace all cations bound to the $-SO_3$ groups in the ionomer material. It is preferred to carry out step (1) in the substantial absence of sunlight (so as to avoid formation of elemental silver). Optionally, $H_2O_2$ can be present in step (1) so as to reoxidize elemental silver which may have inadvertently been formed.

Step (2) can be carried out with the solution obtained in step (1) in any suitable manner, generally at ambient temperature and pressure conditions. Generally, the solution obtained in step (1) is poured over or sprayed onto a porous support material, or the porous support material is impregnated once or several times with the solution. The porous support material can be a plate or a tube of a porous, essentially inert inorganic material, preferably a porous ceramic material, such as a glass frit, or porous sintered alpha- or gamma-alumina, silica, titania, zirconia, zirconia spinel, mullite, cordierite, magnesium alumnate spinel, aluminosilicate(s) or a similar material. These porous ceramic materials are well known and are commercially available as so-called honeycomb monoliths (e.g., from Corning Glass Works, Corning, NY). Generally, the pore size in these ceramic materials is in the range of about 0.01 to about 10 microns, and the open porosity generally is in the range of about 1 to about 65%.

Alternatively, a porous organic polymer material can be employed as the porous support material in step (2). Non-limiting examples of these porous polymer materials are polymer fabrics (such as those made of polymer fibers and glass fibers) or porous plates or diaphragms or tubes which can be made of a polyamide, a polyester, such as poly(ethylene terephthalate), polytetrafluoroethylene (presently preferred), polysulfone, poly(phenylene sulfide), poly(phenylene sulfide sulfone), polystyrene, poly(vinyl butyrate), poly(vinyl chloride), chlorinated poly(vinyl chloride), a cellulose ester, and the like. Generally, the pore size of the polymeric substrate is in the range of about 1 millimicron to about 1 micron.

The ratio of the Ag-exchanged ionomer solution to the porous substrate in step (2) can vary widely, depending on the concentration of the solution, the pore diameter and the percentage of open porosity of the substrate, and the desired thickness of the $Ag^+$-exchanged ionomer film coating. Generally, the weight ratio of the solution to the substrate is such as to provide a thickness of an $Ag^+$-exchanged ionomer coating (on the support material) of about 0.1 to about 300 microns, preferably about 10-100 microns. Generally, the ratio of $Ag^+$ ions to $—SO_3$ groups in the ionomer coating is about 0.5:1 to about 50:1 (preferably about 1:1 to about 40:1).

An optional solvent removal step can be carried out after step (2) in any suitable manner, so as to at least partially remove the solvent used in steps (1) and (2) from the $Ag^+$-exchanged ionomer membrane obtained in step (2). Generally, the solvent is volatile enough to allow the solvent to evaporate at ambient temperature and pressure conditions. However, frequently a separate solvent removal step is not necessary because the solvent generally evaporates to a significant extent during the application of the $Ag^+$-exchanged ionomer membrane in the alkene-alkane separation process described below.

The $Ag^+$-exchanged ionomer membrane prepared by one of the above-described preparation methods is employed in the process for separating gaseous $C_2$-$C_4$ alkenes (monoolefins) from gaseous alkanes, in accordance with this invention. The feed contains at least one $C_2$-$C_4$ alkene (i.e., ethylene, propylene, butene-1, butene-2, isobutylene, mixture of two or more of these alkenes; preferably ethylene) and at least one alkane (such as methane, ethane, propane, n-butane, isobutane, n-pentane, isopentanes, n-hexane, isohexanes, and mixtures thereof; preferably ethane). Generally, the feed gas contains about 2-98 (preferably about 30-70) volume-% alkene(s) and about 2-98 (preferably about 30-70) volume-% alkane(s).

The feed gas must also contain water vapor. If a dry feed gas is used, essentially no advantage of the $Ag^+$-exchanged ionomer membrane of this invention over other, known membranes in an alkene/alkane separation is realized. Preferably, the amount of water vapor present in the feed should be such as to provide a feed which is substantially saturated with water vapor at the operating temperature of the gas separation process of this invention, i.e., the partial pressure of $H_2O$ in the feed is nearly equal to the vapor pressure of water at the operating temperature (e.g., 24 torr $H_2O$ at 25° C.). The term "substantially saturated with water vapor", as used herein, means that the partial pressure of water in the feed gas and in the purge gas, is about 90–100% of the vapor pressure of water at the operating conditions. Preferably, the partial pressure of water is about 100% of the vapor pressure of water at the operating conditions.

Any feed gas which contains $C_2$-$C_4$ alkene(s), alkane(s) and water vapor can be used in the gas separation process of this invention. Suitable feed gases can be natural gas or gaseous refinery streams which have been contacted with water so as to substantially saturate these gases with water vapor at the operating conditions of the separation process of this invention employing the $Ag^+$-exchanged ionomer membrane of this invention. Other gases, besides alkene(s), alkane(s) and water vapor, such as CO, $CO_2$, $N_2$, He, Ar or other noble gases, $O_2$ and diolefins (e.g., butadiene) may also be present in the feed gas, as long as the levels of these additional gases are low enough that they will not substantially interfere with the separation process of this invention.

The gas separation process of this invention can be carried out in any suitable manner. The partial pressure of the alkene(s) on the side of the membrane which is exposed to the feed is higher than the partial pressure of the alkene(s) on the other side of the membrane, and the alkene(s) permeate through the membrane due to the partial pressure difference. Any suitable membrane separation equipment known to those skilled in the art can be employed. Generally, the wet feed gas flows over one side of the $Ag^+$-exchanged ionomer membrane, while a wet inert sweep gas (such as $N_2$) flows along the other side of the membrane and carries off any portion of the feed gas which has permeated through the membrane. Generally, the thin $Ag^+$-exchanged ionomer membrane is supported by a porous support material, preferably a porous inorganic material, such as a glass frit, a metal screen, a ceramic monolith material, porous ceramic tubes, polymer tubes or fibers, and the like.

Any suitable operating conditions can be employed. Generally, the total pressure on the feed side of the membrane is in the range of from about 0.1 to about 100 atm (preferably about 1-5 atm), the total pressure on the sweep gas side of the membrane is in the range of about 1 to about 100 atm (preferably about 1-2 atm). Preferably, the partial pressure difference of the alkene across the membrane is in the range of from about 0.1 to about 10 atm (more preferably about 0.4-3 atm). The operating temperature of the processes of this invention, i.e., the temperature of the feed gas, of the membrane and of the sweep gas during the gas separation process, generally is in the range of from about 0° C. to about 50° C. (preferably about 20°-30° C.).

Even though it is more practical to employ a sweep gas (as described above) to remove permeated gases from the membrane, it is within the scope of this invention to have essentially vacuum conditions on the product side of the membrane and allow the alkene(s) to permeate from the feed compartment through the membrane into the vacuum on the other side of the membrane. When a sweep gas is used, the permeated alkene can thereafter be separated from the sweep gas by any suitable separation means, such as cryogenic distillation and the like.

The following examples are presented to further illustrate the present invention and are not to be considered as unduly limiting the scope of the claimed invention.

EXAMPLE I

This example illustrates the experimental setup for testing the effectiveness of various $Ag^+$ ion-exchanged Nafion ® poly(perfluorosulfonic acid) ionomer membranes for separating ethylene from ethane.

The permeation cell employed in all film tests was a circular stainless steel cell having a diameter of about 8 cm and comprising two narrow compartments (cavities) of about 2 mm height each. A circular Nafion ® membrane (effective area: 12.6 cm$^2$), the thickness of which had been accurately measured, was clamped and sealed between two O-rings in the test cell so as to separate the two compartments. Each compartment of the cell was equipped with a metallic screen support for the membrane and two swagelock ($\frac{1}{8}$") connections (one for the gas inlet and the other one for the gas outlet). A feed gas (generally a mixture of 50 mole-% ethane and 50 mole-% ethylene) flowed through one cell compartment, while a purge gas of pure helium flowed through the other cell compartment (in the same direction as the feed gas). The purge gas picked up ethylene and ethane which had permeated from the feed compartment through the membrane into the purge compartment. The feed gas and the purge gas were introduced into cell compartments at atmospheric pressure. Their flow rates were controlled by means of a Hi-Tec F201C flowmeter and magnetic valves.

Generally, the feed gas rate was about 10 cc/minute and the purge gas rate was about 10 cc/minute. When wet feed and purge gases were used, both gas streams were bubbled through distilled water so as to saturate them with water vapor before they entered the cell compartments. All tests were carried out at about 20°–25° C.

The product gas (i.e., the gas which exited from the purge compartment containing the carrier gas, permeated ethylene and permeated ethane) was passed through a Carlo Erba Gas Chromatograph equipped with a Chrompack fused silica capillary column, a FID detector and a Milton Roy integrator for analyzing relative amounts of permeated ethylene and ethane in the product gas. The concentrations of ethylene and ethane were determined from calibration curves which had earlier been established for each gas in helium. In each gas permeation test, the product gas stream which exited from the test cell was monitored by GC analysis until steady-state conditions were obtained (i.e., until fairly constant ethylene and ethane concentrations were measured).

The flux F of ethylene or ethane through the membrane was calculated from averages of at least five measurements by using the following equation:

$$F = \frac{X \cdot Y}{(1-X) \cdot A},$$

wherein X is the mole fraction of either ethylene or ethane in the product gas (i.e., the purge gas which exited the purge compartment); Y is the flow rate of the purge gas (in mL/second); and A is the effective cross-sectional area (in cm$^2$) of the membrane. All flux test data presented hereinafter for individual membranes have been normalized, i.e., the gas volume (in mL) has been adjusted for S.T.P. conditions (0° C./1 atm.).

The permeability P of each gas was determined by dividing the flux of each gas by the partial pressure differential (driving pressure) of each gas across the membrane and then multiplying the result by the membrane thickness (in cm). The film thickness was measured with a precision micrometer before the membrane was placed in the permeation cell. The average film thickness from at least five independent measurements at different locations on the membrane was used for the calculation of P. The average partial pressure differential (driving pressure) of each gas across the membrane was obtained from the fraction of this gas in the feed, the fraction of this gas in the reject gas (retentate) and the fraction of this gas in the product gas. P values are expressed in barrer units, wherein 1 barrer equals $10^{-10}$ mL·cm/cm$^2$·sec·cm Hg. The separation factor (also called selectivity factor) S was determined by dividing the permeability of ethylene by the permeability of ethane.

EXAMPLE II

This example illustrates the preparation of various $Ag^+$-exchanged Nafion ® perfluorosulfonate ionomer membranes and the effect of specific preparation steps on the performance of these membranes in ethylene/ethane separation processes.

The starting membrane material for all tests was an unreinforced Nafion ® N-117 film (provided by Aldrich Chemical Company, Milwaukee, Wis.) having an average thickness of about 0.2–0.4 mm, a weight caliper (at 20° C., 50% relative humidity) of 3.4 g/dm$^2$, and an equivalent weight (defined above) of about 1100.

Membrane A

This membrane was prepared in accordance with a slightly modified procedure described in Example I in U.S. Pat. No. 4,614,524. A Nafion ® n-117 membrane was first ion-exchanged with Na+ by immersing and heating it in an aqueous 0.15M (0.15 molar) NaOH solution under reflux conditions for 4 hours. The thus-obtained Na+-exchanged membrane was rinsed with water, heated in dry methanol under reflux conditions for 1 hour, and dried in a vacuum desiccator at room temperature for 2.5 days. Thereafter, the Na+-exchanged membrane was immersed in a 1M AgNO$_3$ solution in glycerin for 2 days at room temperature. Thus, the Ag+-exchange and the swelling of the membrane in glycerine were carried out simultaneously.

Membrane A (which had been wiped dry with a paper towel) was tested in accordance with the ethylene/ethane separation procedure of Example I employing a dry equimolar ethylene/ethane feed gas. The flux of ethylene and of ethane through the membrane was $3.5 \cdot 10^{-7}$ mL/cm$^2$·sec and $1.5 \cdot 10^{-8}$ mL/cm$^2$·sec respectively; the average film thickness was 0.22 mm; and the calculated average driving pressure of ethylene and of ethane across the membrane was 38 cm Hg for each gas. The permeability of ethylene and of ethane through Membrane A was calculated to be about 2 barrers and 0.1 barrer, respectively. The separation factor was about 20.

Membrane B

This membrane was prepared substantially in accordance with the procedure of Example I in U.S. Pat. No. 4,614,524. A Nafion ® N-117 membrane was heated in an aqueous 0.15M NaOH solution under reflux conditions for 4 hours. The Na+-exchanged was rinsed with distilled water and heated in dry methanol for 1 hour under reflux conditions. The thus-treated membrane was dried in a vacuum desiccator at room temperature for 1 day, and then immersed in an aqueous 2.1M AgClO$_4$ solution (also containing a small amount of H$_2$O$_2$) for 1 day at room temperature. Then the membrane was rinsed with distilled water and immersed in glycerin for 1 day at room temperature. Thus, the swelling of the membrane in glycerin was carried out after the Ag$^+$-exchange step.

Membrane B (which had been wiped dry with a paper towel) was tested in accordance with the ethylene/ethane separation procedure of Example I employing a wet (i.e., water-saturated) equimolar ethylene/ethane feed gas and a wet He purge gas. The flux of ethylene and ethane through the membrane was 1.6·10$^{-5}$ mL/cm$^2$·sec and 5.0·10$^{-7}$ mL/cm$^2$·sec, respectively; the average film thickness was 0.24 mm; and the calculated average driving pressure of ethylene and ethane across the membrane was 38 cm Hg for each gas. The permeability of ethylene and of ethane through Membrane B was calculated to about 100 barrers and 3 barrers, respectively; and the separation factor was about 30.

Membrane C

This membrane was prepared by the process of this invention comprising a swelling step (at an elevated temperature employing a alcohol) *before* the Ag$^+$-exchange step. A Nafion ® N-117 membrane was heated in an aqueous 0.15M NaOH solution under reflux conditions for 4 hours. The Na$^+$-exchanged membrane was rinsed with distilled water, dried in a vacuum desiccator, and immersed in glycerin which was then heated from room temperature to about 220° C. and thereafter slowly cooled to room temperature. The thus-treated membrane was rinsed with water and immersed in an aqueous 2.1M AgBF$_4$ solution for 3 days at room temperature.

Membrane C (which had been wiped dry with a paper towel) was tested in accordance with the ethylene/ethane separation procedure of Example I employing a water-saturated equimolar ethylene/ethane feed gas and a water-saturated He purge gas. The flux of ethylene and ethane through the membrane was 4.2·10$^{-4}$ mL/cm$^2$·sec and 1.8·10$^{-6}$ mL/cm$^2$·sec, respectively; the average film thickness was 0.30 mm; and the calculated average driving pressure of ethylene and ethane across the membrane was 38 cm Hg for each gas. The average ethylene permeability of ethylene and of ethane through Membrane C was calculated to be about 3,400 barrers and 14 barrers, respectively; and the average separation factor was about 234. Thus, the swelling step in glycerine at an elevated temperature (above 200° C.) before the silver exchange step had a highly beneficial effect on ethylene permeability and the separation factor (as compared with the prior art procedure in accordance with U.S. Pat. No. 4,614,524; Membranes A and B).

Membrane D

This membrane was prepared substantially in accordance with the procedure described for Membrane C, except that after the swelling step in hot glycerin and before the immersion in the aqueous 2M AgBF$_4$ solution, the membrane was immersed in a 1 molar aqueous solution of NaBF$_4$ for 31 days at room temperature (so as to replace a substantial portion of glycerin contained in the swollen Na$^+$-exchanged membrane with water).

Membrane D was tested in accordance with the separation procedure of Example I employing a water-saturated equimolar ethylene/ethane feed gas and a water-saturated purge gas. The flux of ethylene and ethane through the membrane was 1.14·10$^{-3}$ mL/cm$^2$·sec and 1.76·10$^{-6}$ mL/cm$^2$·sec, respectively; the average film thickness was 0.29 mm; and the calculated average driving pressure of ethylene and ethane across the membrane was 34 cm Hg and 38 cm Hg, respectively. The average permeability of ethylene and ethane through Membrane D was calculated to be about 9900 barrers and 13 barrers, respectively; and the average separation factor was about 730. The above test data are considerably higher than those attained for Membrane C. Thus, extensive washing with an aqueous solution before the silver-exchange step had a very beneficial effect on ethylene permeability and the separation factor.

Membrane E

This membrane was prepared substantially in accordance with the procedure for Membrane C, except that an additional heating step in air was carried out before the soaking step in hot glycerin. A Nafion ® N-117 membrane was heated in an aqueous 0.2M NaOH solution under reflux conditions for 4 hours. The Na$^+$-exchanged membrane was rinsed with distilled water and dried in a vacuum desiccator at room temperature for about 16 hours. Thereafter, the membrane was heated at 340° C. in air for about 1 hour and then rapidly cooled in cold nitrogen gas to room temperature and stored in a desiccator for about 1 week. Then the membrane was immersed in glycerin, which was subsequently heated from room temperature to 225° C. and thereafter allowed to slowly cool to room temperature. The swollen membrane was removed from the glycerin, rinsed with water, immersed in an aqueous 0.2M NaOH solution for 4 days, rinsed again with water, and then immersed in an aqueous 6M AgBF$_4$ solution for 2-2.5 days at room temperature.

Membrane E was tested in accordance with the ethylene/ethane separation procedure of Example I employing a wet equimolar mixture of ethylene and ethane and a wet helium purge gas. The flux of ethylene and ethane through the membrane was 1.48·10$^{-3}$ mL/cm$^2$·sec and 1.36·10$^{-6}$·mL/cm$^2$·sec; the average film thickness was 0.33 mm; and the calculated average driving pressure of ethylene and of ethane across the membrane was 38 cm Hg for each gas. The average permeability of ethylene and of ethane through Membrane E was calculated to be about 12,700 barrers and 12 barrers, respectively; and the average separation factor was about 1000. A second Membrane E was tested in a separate test, as described above. Test results for this second Membrane E were: flux of ethylene and ethane through the membrane was 2.47·10$^{-3}$ mL/cm$^2$·sec and 1.2·10$^{-6}$ mL/cm$^2$·sec, respectively; the average film thickness was 0.32 mm; the calculated average driving pressure of ethylene and ethane was 32 cm Hg and 38 cm Hg, respectively; the average permeability of ethylene and of ethane across the membrane was calculated to be 24,000 barrers and 10 barrers, respectively; and the separation factor was about 2,400. A comparison of these test data with the corresponding data for Membrane C indicate an increase of both ethylene permeability and separation factor caused by a combination of the additional heating step before the swelling in hot glycerin and a higher AgBF$_4$ concentration (6M for Membrane E vs. 2.1M for Membrane C).

A membrane labeled Membrane E* which was prepared substantially in accordance with the procedure of Membrane E (except that the solution used in the Ag$^+$ ion-exchange step was 1M AgBF$_4$ in glycerin) was tested with a *dry* feed gas and a *dry* He purge gas. The flux of ethylene and ethane through the membrane was $4.1 \cdot 10^{-7}$ mL/cm$^2$·sec and $1.0 \cdot 10^{-8}$ mL/cm$^2$·sec, respectively; the average film thickness was 0.32 mm; and the calculated average driving pressure of ethylene and of ethane across the membrane was 38 cm Hg for each gas. The permeability of ethylene and of ethane was calculated to be 3 barrers and 0.1 barrer respectively; and the separation factor was about 30. These test data demonstrate that the ethylene/ethane separation process in accordance with this invention requires the presence of water vapor in the feed gas in order to attain high ethylene permeability and high selectivity.

Membrane F

This membrane was prepared substantially in accordance with the procedure for Membrane E, except that the membrane, after it had been swollen in hot glycerin, was washed in an aqueous solution of NaBF$_4$ for about 20 days (rather than in 0.2 NaOH for 4 days) and was then immersed in an aqueous 2M AgBF$_4$ solution for 25 days (rather than in 6M AgBF$_4$ for 2.5 days) at room temperature.

Membrane F was tested in accordance with the separation method of Example I. The flux of ethylene and ethane was $1.36 \cdot 10^{-3}$ mL/cm$^2$·sec and $1.55 \cdot 10^{-6}$ mL/cm$^2$·sec, respectively; the average film thickness was 0.26 mm; and the calculated average driving pressure of ethylene and of ethane across the membrane was 31 cm Hg and 38 cm Hg, respectively. The average permeability of ethylene and of ethane through Membrane F was calculated to be 11,300 barrers and 11 barrers, respectively; and the separation factor was about 1000. A comparison with the test results obtained for Membrane C clearly indicate that a prolonged contact with the Ag$^+$ ion-exchange solution (which probably results in a greater concentration of Ag$^+$ in the Ag$^+$-exchanged membrane) had a very beneficial effect on both ethylene permeability and selectivity.

The most pertinent above-described test results are summarized in Table I.

TABLE I

| Test | Membrane | Water Present In Feed Gas and Purge Gas | Average Ethylene Permeability (Barrers) | Average Separation Factor |
|---|---|---|---|---|
| 1 (Control) | A | No | 2 | 20 |
| 2 (Control) | B | Yes | 100 | 30 |
| 3 (Invention) | C | Yes | 3,400 | 230 |
| 4 (Invention) | D | Yes | 9,900 | 730 |
| 5 (Invention) | E | Yes | 18,600[1] | 1,700[1] |
| 6 (Control) | E* | No | 3 | 30 |
| 7 (Invention) | F | Yes | 11,300 | 1,000 |

[1]average of two duplicate runs

The above-summarized test results clearly demonstrate the highly beneficial effects of the step of swelling the membrane in hot alcohol (glycerin) *before* the silver ion-exchange step (Membranes C, D, E and F versus Membrane B). Furthermore, a comparison of the tests carried out with Membranes E and E* dramatically demonstrates the necessity of the presence of water vapor during the separation process so as to attain high ethylene flux and high selectivity. The beneficial effect of carrying out a heating/quenching step before the swelling step (in glycerin at an elevated temperature) is also demonstrated (Membranes E and F versus Membrane C). A comparison of the test data for Membranes D and C demonstrates the beneficial effect of extensive washing of the swollen membrane in an aqueous solution before the Ag$^+$-exchange step.

Test results for a wet propylene containing feed (not described herein in detail) indicate that the permeability of propylene through several invention membranes was about 5000–7000 barrers, thus comparable to the permeability of ethylene through these membranes. Based on these preliminary test results, it is concluded that the separation of propylene from gaseous alkanes in accordance with this invention will yield results similar to those obtained for the ethylene/ethane separation.

EXAMPLE III

This example illustrates the preparation of a Ag$^+$-exchanged Nafion ® perfluorosulfonate ionomer membrane consisting essentially of an alkali-metal exchange step and a silver exchange step without any prior or simultaneous swelling of the alkali-metal-exchanged membrane with an alcohol.

Control Membrane G was prepared heating a Nafion ® N-117 membrane in an aqueous 0.2M NaOH solution under reflux conditions for 4 hours. The Na$^+$-exchanged membrane was allowed to cool to room temperature, rinsed with water and immersed in an aqueous 1M NaBF$_4$ solution for 64 hours. Invention Membrane H was prepared by immersing Membrane G in an aqueous 1M AgBF$_4$ solution for 6 days. Both membranes were tested in accordance with the procedure described in Example I, employing a water-saturated equimolar ethylene/ethane feed and a water-saturated He purge gas.

Test results for Control Membrane G were as follows: flux of ethylene and ethane through the membrane was $1.1 \cdot 10^{-6}$ mL/cm$^2$·sec and $4.2 \cdot 10^{-7}$ mL/cm$^2$·sec, respectively; the average film thickness was 0.21 mm; the calculated driving pressure of ethylene and ethane across the membrane was 38 cm Hg for each gas; the permeability of ethylene and ethane through Membrane G was calculated to be 6 barrers and 2 barrers, respectively; and the separation factor was about 3.

Test results for Invention Membrane H were as follows: the flux of ethylene and ethane through the membrane was $2.2 \cdot 10^{-4}$ mL/cm$^2$·sec and $3.9 \cdot 10^{-7}$ mL/cm$^2$·sec, respectively; the average film thickness was 0.21 mm; the calculated driving pressure of ethylene and ethane across the membrane was 37 cm Hg and 38 cm Hg, respectively; the permeability of ethylene and ethane through membrane H was calculated to be 1253 barrers and 2.16 barrers, respectively; and the separation factor was about 580. These test results for Membranes H and G demonstrate the significant effect of the Ag$^+$ ion-exchange step on the ethylene permeability and the selectivity factor. Furthermore, a comparison of test results for Invention Membrane H and for prior art Membranes A and B, described in Example II, demonstrate the significant superiority of Membrane H.

EXAMPLE IV

This example illustrates the preparation and use of $Ag^+$-exchanged hollow fibers of Nafion ® polyfluorosulfonate ionomer. Hollow fibers of Nafion ® (supplied by Perma Pure Products, Inc., Tom's River, N.J., under the product designation of Nafion ® tubing size 020) having an inner diameter of 0.33 mm and an outer diameter of 0.51 mm were heated for 4 hours under reflux conditions in an aqueous 0.2M NaOH solution. The $Na^+$-exchanged Nafion ® fibers were washed with distilled water, heated in an oven to 250° C. during a time period of 70 minutes, and rapidly cooled (quenched) with cold nitrogen gas to room temperature. The fibers were then immersed in glycerin which was heated to 225° C. and thereafter slowly cooled to room temperature. The swollen fibers were washed with distilled water and immersed in an aqueous 0.2M NaOH solution for about 2 days (so as to replace a substantial portion of glycerin present in the swollen membrane with water).

The thus-treated Nafion ® fibers were then mounted and glued in the inlet and outlet gaskets of a stainless steel permeator having a length of 24.5 cm and an inner diameter of 1 cm. The shell compartment (equipped with an inlet and an outlet for the purge gas) of the permeator was filled with distilled water during the mounting procedure. After the fibers had been mounted, the water in the shell compartment was replaced with an aqueous 1M $AgBF_4$ solution. The mounted Nafion ® fibers remained in contact with the $AgBF_4$ solution at room temperature for about 2–3 days.

After the aqueous $AgBF_4$ had been removed from the shell compartment, the $Ag^+$-exchanged Nafion ® fibers were tested for ethylene/ethane separation. A water-saturated equimolar ethylene/ethane feed mixture flowed through the mounted $Ag^+$-exchanged Nafion ® fibers at a rate of about 10 ml/minute, while a water-saturated purge gas of helium flowed through the shell compartment (perpendicular to the direction of the feed gas) around the outer walls of the mounted fibers at a flow rate of 5 ml/minute. The amounts of ethylene and ethane which had permeated through the $Ag^+$-exchanged Nafion ® fiber walls were measured by means of a gas chromatograph (as described in Example I). Ethylene permeability and the selectivity factor were determined in accordance with the procedure outlined in Example I.

The flux of ethylene and of ethane through the walls of the $Ag^+$-exchanged Nafion ® fibers, determined in six different tests, ranged from $2.5 \cdot 10^{-3}$ to $3.4 \cdot 10^{-3}$ mL/$cm^2$·sec and $9.4 \cdot 10^{-6}$ to $1.5 \cdot 10^{-5}$ mL/$cm^2$·sec, respectively; the film thickness (original fiber wall thickness) was about 90 microns; and the calculated average driving pressure of ethylene and of ethane across the fiber wall was about 33–38 cm Hg and about 38 cm Hg, respectively. The average calculated permeability of ethylene and of ethane was about 6700–9400 barrers and about 20–35 barrers, respectively; and the separation factor was about 200. Thus, the ethylene permeability and separation factors were of the same order of magnitude as those attained with flat $Ag^+$-exchanged Nafion ® Membranes C and D (described in Example II).

EXAMPLE V

This example illustrates the preparation and use of $Ag^+$-exchanged Nafion ® polyfluorosulfonate ionomer coatings on porous supports.

Membrane I was prepared by filling a porous alumina tube (having an average pore diameter of 200 nanometers, an inner tube diameter of 7 mm, an outer tube diameter of 10 mm and a length of 2.21 cm; commercially available from Aluminum Company of America, Pittsburgh, PA, under the product designation of Membralox ®) with a solution of a $Ag^+$-exchanged Nafion ® ionomer. This solution was prepared by mixing (a) 3.5 g of a 5 weight-% solution of Nafion ® EW 1100 (supplied by Aldrich Chemical Company, St. Louis, MO; equivalent weight: 1100) in a lower alcohol/$H_2O$ solvent (weight ratio: about 9:1), (b) 0.896 g $AgBF_4$ and (c) 0.8 g $H_2O_2$ (which is present to prevent the formation of elemental silver). The thus-prepared solution had a ratio of gram-atoms $Ag^+$ to gram-equivalents of $-SO_3^-$ groups present in the ionomer of about 29:1. The alumina tube containing this solution was shaken several times, the solution was poured out, and $N_2$ gas was flushed through the tube. This coating procedure was repeated four times. The thus-coated alumina tube was stored in the dark at room temperature for about 16 hours.

Membrane J was prepared by pouring a solution of $Ag^+$-exchanged Nafion ® onto a polytetrafluoroethylene (PTFE) filter (supplied by Micron Separations, Inc., under the catalog no. F02LPO4700; having an average pore size of about 0.2 micrometers and a diameter of 47 mm). The $Ag^+$-exchanged Nafion ® solution had been prepared by mixing 3.5 g of the 5 weight-% Nafion ® EW 1100 solution (described above) with 1.402 g $AgClO_4$ and a few drops of aqueous 30 weight-% $H_2O_2$. The $Ag^+$-exchanged Nafion ® solution had a ratio of $Ag^+$ gram-atoms to $-SO_3^-$ gram-equivalents in the ionomer of about 42:1. The PTFE filter and the Nafion ®/$AgClO_4$ solution (which had been cast upon the filter) were kept at room temperature in the dark for about two days.

Membrane I was tested in the permeator cell described in Example IV employing a water-saturated equimolar ethylene/ethane feed and a water-saturated He purge gas. The flux of ethylene and of ethane through Membrane G was $2.07 \cdot 10^{-3}$ mL/$cm^2$·sec and $1.57 \cdot 10^{-6}$ mL/$cm^2$·sec, respectively; the membrane thickness was estimated to be at least 0.02 mm; the average driving force of ethylene and of ethane was about 21 cm Hg and about 38 cm Hg, respectively; the calculated average permeability of ethylene and ethane through Membrane I was at least about 2000 barrers and 1 barrer, respectively; and the separation factor was about 2000.

Membrane J was tested in accordance with the procedure described in Example I employing a water saturated equimolar ethylene/ethane feed gas and a water-saturated the purge gas. Test results were: the flux of ethylene and of ethane through Membrane J was $1.45 \cdot 10^{-3}$ mL/$cm^2$·sec and $8.5 \cdot 10^{-7}$ mL/$cm^2$·sec, respectively; the film thickness was estimated to be at least 0.03 mm; the average driving pressure of ethylene and of ethane across the membrane was about 30 cm Hg and about 38 cm Hg, respectively; the calculated average permeability ethylene and ethane through Membrane J was at least about 1400 barrers and 0.7 barrer, respectively; and the separation factor was about 2000.

Thus, ethylene permeabilities and separation factors determined for Membranes I and J were in the same order of magnitude as those obtained for invention Membranes C-F (Example II) and invention Membrane H (Example III).

Reasonable variations and modifications are possible within the scope of the disclosure of this invention and the appended claims.

That which is claimed is:

1. In a process for separating at least one alkene containing 2 to 4 carbon atoms per molecule from at least one alkane containing 1 to 6 carbon atoms per molecule contained in a gaseous feed by means of an ionomer membrane, the improvements which comprise:

having water vapor present in said gaseous feed, and using a silver-exchanged ionomer membrane having been prepared by the preparation method comprising the steps of (a) contacting (i) an ionomer membrane of a copolymer of tetrafluoroethylene and at least one perfluorovinyl ether containing a terminal sulfonic acid group with (ii) a solution of at least one alkali metal compound, under such conditions as to obtain an alkali-metal-exchanged ionomer membrane;

(b) contacting the thus-obtained alkali-metal-exchanged ionomer membrane with a liquid comprising at least one alcohol containing from 2 to 20 carbon atoms and from 1 to 5 hydroxyl groups per molecule, under such conditions as to obtain a swollen alkali-metal-exchanged ionomer membrane; and (c) treating the thus-obtained swollen alkali-metal-exchanged ionomer membrane with a solution containing at least one silver compound, under such conditions as to replace alkali metal ions with silver ions in said ionomer membrane.

2. A process in accordance with claim 1, wherein said gaseous feed is substantially saturated with water vapor at the operating conditions of said process.

3. A process in accordance with claim 2, wherein said at least one alkene contained in said gaseous feed is ethylene and said at least one alkane contained in said gaseous feed is ethane.

4. A process in accordance with claim 1, wherein said copolymer of said ionomer membrane used in step (a) has an equivalent weight of about 500-2000.

5. A process in accordance with claim 1, wherein said contacting in step (a) is carried out for about 0.5 to about 50 hours at a temperature of about 30°-100° C.

6. A process in accordance with claim 1, wherein said preparation method additionally comprises steps (a1) separating the alkali-metal-exchanged ionomer membrane obtained in step (a) from the solution of at least one alkali metal compound used in step (a), and (a2) heating the separated alkali-metal-exchanged membrane obtained in step (a1) at a temperature in the range of from about 100° to about 350° C. for a time period in the range of about 1 minute to about 3 hours and thereafter cooling the thus-heated membrane to a temperature of about 10°-50° C. at a rate of about 1°-5° C. per second; and wherein step (b) is carried out with the alkali-metal-exchanged membrane having undergone the treatment of step (a2).

7. A process in accordance with claim 6, wherein said heating in step (a2) is carried out for a time period of about 1-2 hours at a temperature of about 330°-350° C.

8. A process in accordance with claim 1, wherein step (b) is carried out for a time period of at least about 0.1 hour at a temperature in the range of about 75° C. to the normal boiling point of said at least one alcohol.

9. A process in accordance with claim 8, wherein said time period is in the range of about 1 hour to about 50 hours.

10. A process in accordance with claim 8, wherein said at least one alcohol is at least one polyhydric alcohol.

11. A process in accordance with claim 10, wherein said at least one polyhydric alcohol is glycerin.

12. A process in accordance with claim 8, wherein step (b) is carried out with glycerin for a time period of about 1 hour to about 50 hours at a temperature of about 200° C. to about 290° C.

13. A process in accordance with claim 1, wherein said at least one silver compound contained in said solution used in step (c) is selected from the group consisting of $AgNO_3$, $AgClO_4$ and $AgBF_4$.

14. A process in accordance with claim 1, wherein the silver concentration in said solution employed in step (c) is in the range of about 0.5 to about 6 gram-equivalents $Ag^+$ per liter.

15. A process in accordance with claim 1 comprising the additional step (c1) of separating the silver-exchanged ionomer membrane obtained in step (c) from said solution of at least one silver compound.

16. In a process for separating at least one alkene containing 2 to 4 carbon atoms per molecule from at least one alkane containing 1 to 6 carbon atoms per molecule contained in a gaseous feed by means of an ionomer membrane, the improvements comprise:

having water vapor present in said gaseous feed, and using a silver-exchanged ionomer membrane having been prepared by the preparation method consisting essentially of the steps of (A) contacting (i) an ionomer membrane of a copolymer of tetrafluoroethylene and a perfluorovinyl ether containing a terminal sulfonic acid group with (ii) a solution consisting essentially of at least one alkali metal and water, under such conditions as to obtain an alkali-metal-exchanged ionomer membrane, and (B) treating the alkali-metal exchanged ionomer membrane obtained in step (A) with a solution consisting essentially of at least one silver compound and water, under such conditions as to obtain a substantially silver-exchanged ionomer membrane.

17. A process in accordance with claim 21, wherein said gaseous feed is substantially saturated with water vapor at the operating conditions of said process.

18. A process in accordance with claim 17, wherein said at least one alkene contained in said gaseous feed is ethylene and said at least one alkane contained in said gaseous feed is ethane.

19. A process in accordance with claim 16, wherein said copolymer of said ionomer membrane used in step (A) has an equivalent weight of about 500-2000.

20. A process in accordance with claim 16, wherein said contacting in step (A) is carried out for about 0.5 to about 50 hours at a temperature of about 30°-100° C.

21. A process in accordance with claim 16, wherein said at least one alkali metal is sodium.

22. A process in accordance with claim 16, wherein said at least one silver compound contained in said solution used in step (B) is selected from the group consisting of $AgNO_3$, $AgClO_4$ and $AgBF_4$.

23. A process in accordance with claim 16, wherein the silver concentration in said solution employed in step (B) is in the range of about 0.5 to about 6 gram-equivalents $Ag^+$ per liter.

24. In a process for separating at least one alkene containing 2 to 4 carbon atoms per molecule from at least one alkane containing 1 to 6 carbon atoms per molecule contained in a gaseous feed by means of an ionomer membrane, the improvements comprise:

having water vapor present in said gaseous feed, and using a silver-exchanged ionomer membrane having been prepared by the preparation process consisting essentially of the steps of (1) mixing ($\alpha$) a solution of a copolymer of tetrafluoroethylene and a perfluorovinyl ether containing a terminal sulfonic acid group and ($\beta$) at least one silver compound, under such conditions to obtain a solution comprising a silver-exchanged copolymer;

(2) coating a porous support material with the solution obtained in step (1); and (3) removing solvent contained in the solution used in step (2) from the coated porous support material obtained in step (2).

25. A process in accordance with claim 24, wherein said gaseous feed is substantially saturated with water vapor at the operating conditions of said process.

26. A process in accordance with claim 25, wherein said at least one alkene contained in said gaseous feed is ethylene and said at least one alkane contained in said gaseous feed is ethane.

27. A process in accordance with claim 24, wherein said copolymer used in step (a) has an equivalent weight of about 500-2000.

28. A process in accordance with claim 24, wherein the concentration of said copolymer employed in step (1) is in the range of about 0.1 to about 10 weight percent, and the ratio of gram-equivalents of silver to gram-equivalents of $-SO_3H$ groups in said copolymer is in the range of about 0.5:1 to about 50:1.

29. A process in accordance with claim 28, wherein said ratio is in the range of about 1:1 to about 40:1.

30. A process in accordance with claim 24, wherein said porous support material used in step (2) is an inorganic material selected from the group consisting of glass frits, sintered alumina, silica, titania, zirconia, zirconia spinel, mullite, cordierite, magnesium aluminate spinel and aluminosilicates.

31. A process in accordance with claim 30, wherein said support material is a porous alumina tube.

32. A process in accordance with claim 24, wherein the porous support material used in step (2) is made of an organic polymer material.

33. A process in accordance with claim 32, wherein said organic polymer material is polytetrafluoroethylene.

34. In a process for separating at least one alkene containing 2 to about 4 carbon atoms per molecule from at least one alkane containing 1 to 6 carbon atoms per molecule contained in a gaseous feed by means of an ionomer membrane, the improvements which comprise:

having water vapor present in said gaseous feed, and using a silver-exchanged ionomer membrane having been prepared by the preparation method comprising the steps of (a) contacting (i) an ionomer membrane of a copolymer of tetrafluoroethylene and at least one perfluorovinyl ether containing a terminal sulfonic acid group with (ii) a solution of at least one alkali metal compound, under such conditions as to obtain an alkali-metal-exchanged ionomer membrane;

(b) contacting the thus-obtained alkali-metal-exchanged ionomer membrane with a liquid comprising at least one alcohol containing from 2 to 20 carbon atoms and from 1 to 5 hydroxyl groups per molecule, under such conditions as to obtain a swollen alkali-metal-exchanged ionomer membrane;

(b1) separating the swollen alkali-metal-exchanged ionomer membrane obtained in step (b) from said at least one alcohol used in step (b);

(b2) immersing the separated swollen alkali-metal-exchanged ionomer membrane obtained in step (b1) in water or, alternatively, in an aqueous solution of an alkali metal compound, for a period of time in the range of about 0.5 day to about 50 days; and (c) treating the swollen alkali-metal-exchanged ionomer membrane having undergone the treatment of step (b2) with a solution containing at least one silver compound, under such conditions as to replace alkali metal ions with silver ions in said ionomer membrane.

35. A process in accordance with claim 34, wherein said gaseous feed is substantially saturated with water vapor at the operating conditions of said process.

36. A process in accordance with claim 35, wherein said at least one alkene contained in said gaseous feed is ethylene and said at least one alkane contained ins aid gaseous feed is ethane.

37. A process in accordance with claim 34, wherein said copolymer of said ionomer membrane used in step (a) has an equivalent weight of about 500-2000.

38. A process in accordance with claim 34, wherein said contacting in step (a) is carried out for about 0.5 to about 50 hours at a temperature of about 30°-100° C.

39. A process in accordance with claim 34, wherein step (b) is carried out for a time period of at least about 0.1 hour at a temperature in the range of about 75° C. to the normal boiling point of said at least one alcohol.

40. A process in accordance with claim 39, wherein said time period is in the range of about 1 hour to about 50 hours.

41. A process in accordance with claim 39, wherein said at least one alcohol is at least one polyhydric alcohol.

42. A process in accordance with claim 41, wherein said at least one polyhydric alcohol is glycerin.

43. A process in accordance with claim 39, wherein step (b) is carried out with glycerin for a time period of about 1 hour to about 50 hours at a temperature of about 200° C. to about 290° C.

44. A process in accordance with claim 34, wherein step (b2) is carried out with water.

45. A process in accordance with claim 34, wherein step (b2) is carried out with an aqueous 0.1-2 molar solution of at least one alkali metal compound.

46. A process in accordance with claim 45, wherein said alkali metal is sodium.

47. A process in accordance with claim 34, wherein said at least one silver compound contained in said solution used in step (c) is selected from the group consisting of $AgNO_3$, $AgClO_4$ and $AgBF_4$.

48. A process in accordance with claim 34, wherein the silver concentration in said solution employed in step (c) is in the range of about 0.5 to about 6 gram-equivalents $Ag^+$ per liter.

49. A process in accordance with claim 34, comprising the additional steps of (a1) separating the alkali-metal-exchanged ionomer membrane obtained in step (a) from the solution of at least one alkali metal compound used in step (a), and (a2) heating the separated alkali-metal-exchanged membrane obtained in step (a1) at a temperature in the range of from about 100° to about 350° C. for a period fo time in the range of about 1 minute to about 3 hours and thereafter cooling the thus-heated membrane to a temperature of about 10°–50° C. at a rate of about 1°–5° C. per second; and wherein step (b) is carried out with the alkali-metal-exchanged ionomer membrane having undergone the treatment of step (a2).

50. A process in accordance with claim 49, wherein said heating in step (a2) is carried out for a time period of about 1–2 hours at a temperature of about 330°–350° C.

51. A process in accordance with claim 34, comprising the additional step (c1) of separating the silver-exchanged ionomer membrane obtained in step (c) from said solution of at least one silver compound.

* * * * *

UNITED STATES PATENT AND TRADEMARK OFFICE
CERTIFICATE OF CORRECTION

PATENT NO. : 5,191,151
DATED : March 2, 1993
INVENTOR(S) : Odd I. Eriksen et al.

It is certified that error appears in the above-identified patent and that said Letters Patent is hereby corrected as shown below:

Title page, left column, item [73], add --- Norway --- after "Company".

Claim 17, column 18, line 52, delete "21" and substitute --- 16 --- therefor.

Claim 49, column 21, line 14, delete "fo" after "period" and substitute --- of --- therefor.

Signed and Sealed this

Twenty-fifth Day of May, 1993

Attest:

MICHAEL K. KIRK

*Attesting Officer*   *Acting Commissioner of Patents and Trademarks*